United States Patent [19]
Littmann et al.

[11] Patent Number: 5,509,411
[45] Date of Patent: Apr. 23, 1996

[54] INTRAVASCULAR SENSING DEVICE

[75] Inventors: Laszlo Littmann, Charlotte, N.C.; Gene Samson, Fremont; Gabriel Vegh, Alamo, both of Calif.

[73] Assignee: Cardima, Inc., Fremont, Calif.

[21] Appl. No.: 188,619

[22] Filed: Jan. 27, 1994

Related U.S. Application Data

[63] Continuation-in-part of Ser. No. 10,818, Jan. 29, 1993, Ser. No. 43,449, Apr. 5, 1993, abandoned, and Ser. No. 57,294, May 5, 1993, abandoned.

[51] Int. Cl.$^6$ .................................................. A61B 5/04
[52] U.S. Cl. ........................................ 128/642; 128/772
[58] Field of Search .................................. 128/642, 692, 128/693, 772; 607/116, 119, 122–125, 126, 127

[56] References Cited

U.S. PATENT DOCUMENTS

| | | | |
|---|---|---|---|
| Re. 33,925 | 5/1992 | Bales et al. | 606/48 |
| 4,481,953 | 11/1984 | Gold et al. | 128/642 |
| 4,690,155 | 9/1987 | Hess . | |
| 4,777,955 | 10/1988 | Brayton et al. | 128/642 |
| 4,785,815 | 11/1988 | Cohen et al. | 128/642 |
| 4,840,186 | 6/1989 | Lekholm et al. | 607/122 |

(List continued on next page.)

FOREIGN PATENT DOCUMENTS

| | | | |
|---|---|---|---|
| 0369044 | 5/1990 | European Pat. Off. | 607/122 |
| 0387453 | 9/1990 | European Pat. Off. . | |
| 1813232 | 6/1969 | Germany | 607/116 |
| 3718139C1 | 12/1988 | Germany . | |
| WO80/02801 | 12/1989 | WIPO . | |
| WO90/03151 | 4/1990 | WIPO . | |
| WO92/21278 | 10/1992 | WIPO . | |
| WO94/06349 | 3/1994 | WIPO . | |

OTHER PUBLICATIONS

Swartz, M. D., et al., Endocardial Atrial Catheter Ablation of Accessory Pathways After Intravascular Localization. NASPE Abstracts, *PACE*, vol. 13, Apr. 1990, p. 527, Abstract 126.
Fisher et al., "Nonsurgical Electrical Ablation of Tachycardias: Importance of Prior in Vitro Testing of Catheter Leads," *PACE* (1984) 7:74–81.
Brugada, et al., "Termination of Tachycardias by Interrupting Blood Flow to the Arrhythmogenic Area," *Am. J. Cardiology* (1988) 62:387–392.
Walter, et al., Europ. Surg. Res. 3:130–138 (1971).
Brugada, et al., "Transcordary Chemical Ablation of Ventricular Tachycardia," *Circulation* (1989) 79:475–482.
Lawrence T. Weston, M. D., et al., "A Prototype Coronary Electrode Catheter for Intracoronary Electrogram Recording," *The American Journal of Cardiology*, vol. 70, Dec. 1, 1992, pp. 1492 and 1493.
Repetto, et al., Transcoronary Epicardial Mapping of Accessory Pathways. Implications for Ablation Techniques. 10th Int'l. Cong., "The New Frontiers of Arrthythmias." Marilleva, Italy. Jan. 25–Feb. 1 1992. pp. 475–480.
Lesh, M. D. et al., Mapping in the Right Coronary Artery as an Aid to Radiofrequency Ablation of Right-Sided Accessory Pathways. NASPE Abstracts. *PACE*, vol. 14, Apr. 1991, Part II, p. 671, Abstract 213.
Weston et al., "A Prototype Coronary Electrode Catheter for Intra Coronary Electsogram Recording", American Journal of Cardiology, vol. 70, Dec. 1, 1992.

*Primary Examiner*—William E. Kamm
*Assistant Examiner*—Jeffrey R. Jastrzab
*Attorney, Agent, or Firm*—Crosby, Heafey, Roach & May

[57] ABSTRACT

A system for detecting electrical activity within a patient's heart comprising an elongated intravascular device, such as a catheter or guidewire, having at least one bipolar electrode pair on a distal section of the elongated device to intravascularly detect electrical activity within the patient's heart. The catheter or guidewire preferably has a tubular shaft formed of braided strands which include a plurality of insulated conductors which are electrically connected to the bipolar electrodes.

48 Claims, 10 Drawing Sheets

U.S. PATENT DOCUMENTS

| | | | |
|---|---|---|---|
| 4,867,173 | 9/1989 | Leoni | 128/772 |
| 4,869,248 | 9/1989 | Narula | 128/303.13 |
| 4,945,912 | 8/1990 | Langberg | 128/642 |
| 4,957,110 | 9/1990 | Vogel et al. . | |
| 4,966,597 | 10/1990 | Cosman | 606/50 |
| 4,979,510 | 12/1990 | Franz et al. | 128/642 |
| 5,044,375 | 9/1991 | Bach, Jr. et al. . | |
| 5,056,517 | 10/1991 | Fenici et al. . | |
| 5,083,565 | 1/1992 | Parins | 128/642 |
| 5,095,916 | 3/1992 | Smits . | |
| 5,095,917 | 3/1992 | Vancaillie | 128/831 |
| 5,099,838 | 3/1992 | Bardy . | |
| 5,122,136 | 6/1992 | Gugleilmi et al. | 606/32 |
| 5,125,896 | 6/1992 | Hojeibane . | |
| 5,140,987 | 8/1992 | Schuger et al. . | |
| 5,159,937 | 11/1992 | Tremulis | 128/772 |
| 5,165,403 | 11/1992 | Mehra . | |
| 5,170,802 | 12/1992 | Mehra . | |
| 5,174,288 | 12/1992 | Bardy et al. . | |
| 5,184,621 | 2/1993 | Vogel et al. | 128/642 |
| 5,193,546 | 3/1993 | Vogel et al. . | |
| 5,193,550 | 3/1993 | Duffin | 128/697 |
| 5,364,352 | 11/1994 | Cimino et al. | 604/95 |

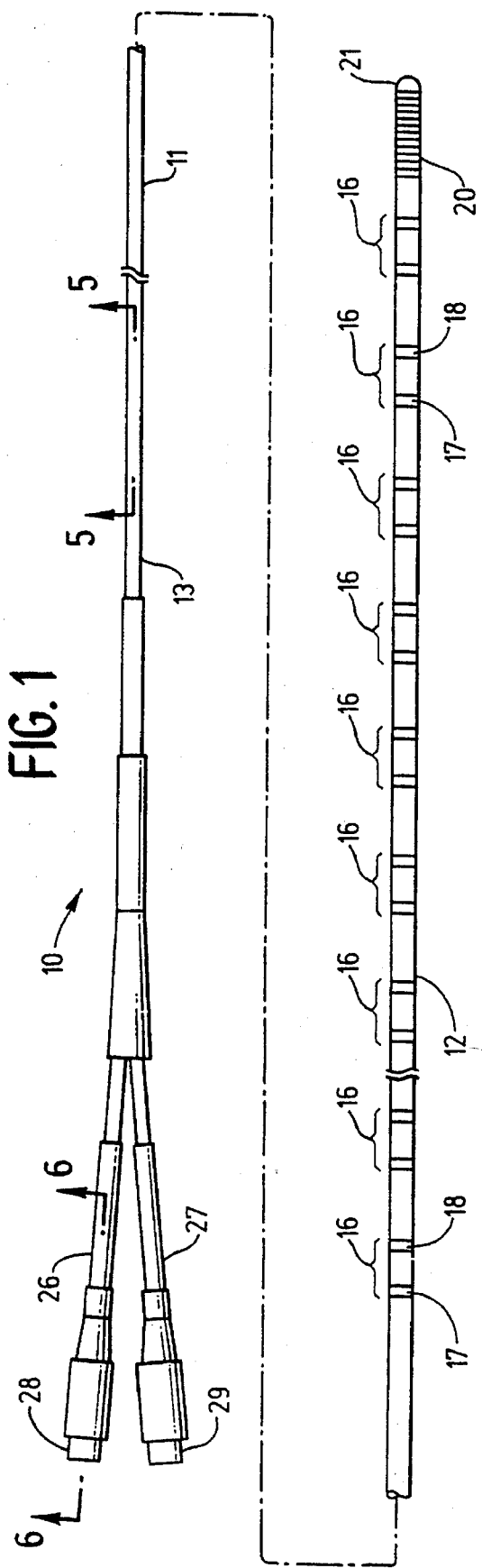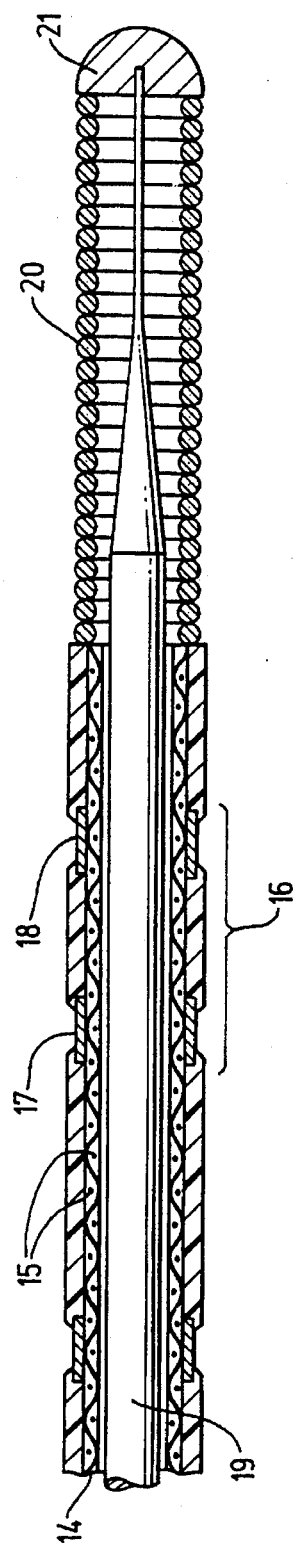

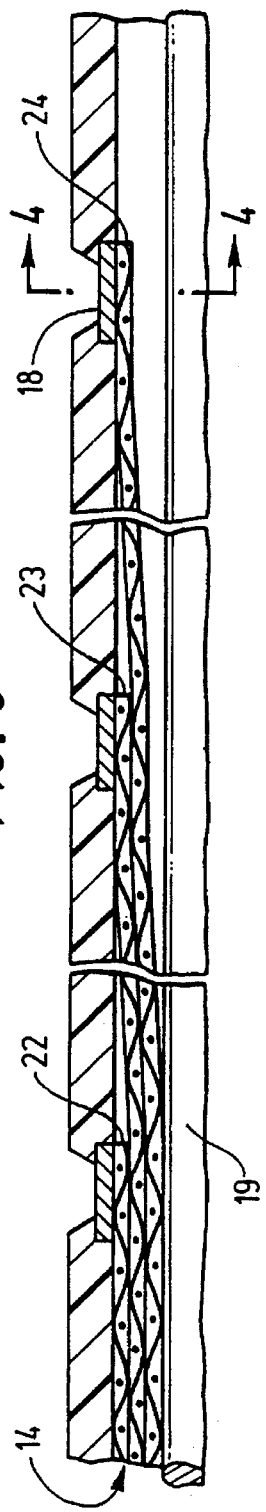
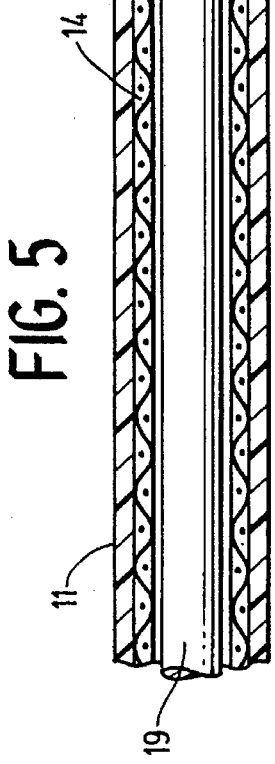
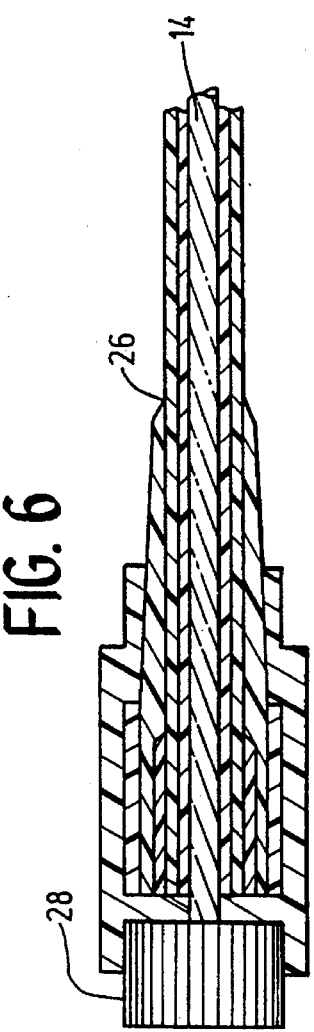
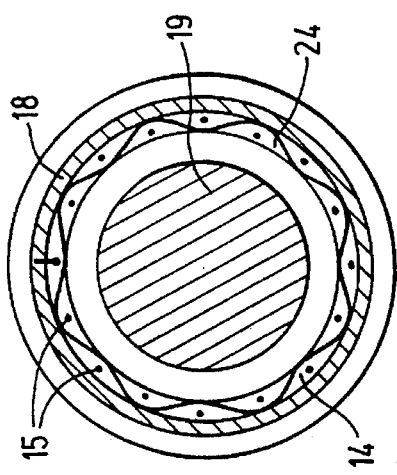

INTRAVASCULAR SENSING DEVICE

RELATED APPLICATIONS

This application is a continuation-in-part application of application Ser. No. 08/010,818, filed Jan. 29, 1993, application Ser. No. 08/043,449, filed Apr. 5, 1993, now abandoned, and application Ser. No. 08/057,294, filed May 5, 1993, now abandoned, which are incorporated herein in their entirety by reference.

BACKGROUND OF THE INVENTION

This invention generally relates to the detection of electrical activity or signals within a patient's heart and particularly for determining the source of signals causing arrhythmia.

Prior methods for treating a patient's arrhythmia include the use of antiarrhythmic drugs such as sodium and calcium channel blockers or drugs which reduce the Beta-adrenergic activity. Other methods include the surgically sectioning the origin of the signals causing the arrhythmia or the conducting pathsray for such signals. More frequently, however, to terminate the arrhythmia, the heart tissue which causes the arrhythmia is destroyed by heat, e g. applying a laser beam or radio frequency (RF) energy to a desired location on the patient's endocardium.

In the latter instance, the location of the site causing the arrhythmia must be accurately known in order to be able to contact the desired location with a tissue destroying device. A major problem of ablating the site of the origin of the signals or a conductive pathway is to accurately determine the site so that an excessive amount of good tissue is not destroyed along with the arrhythmogenic site to ensure that the arrhythmia does not return. For example, the average arrhythmogenic site consists of about 1.4 $cm^2$ of endocardial tissue, whereas a re-entrant site might be much larger. RF ablation techniques produce lesions about 0.5 $cm^2$ in diameter, so several lesions may have to be formed to completely ablate the area of interest if the arrhythmogenic or re-entrant site is not accurately mapped, much good tissue surrounding the site will be unnecessarily destroyed.

A variety of methods have been used to detect electrical activity within a patient's heart to facilitate the mapping of electrical activity causing the arrhythmia. A number of U.S. Patents describe the use of elongated intravascular signed sensing devices which are advanced through the patient's vasculature until the distal portions of the sensing devices are disposed within one of the heart chambers with one or more electrodes on the distal portion in contact with the endocardial lining. While this procedure is widely used, it does not always allow the site of arrhythmogenic signals to be accurately determined.

The literature also mentions advancing an intravascular signal sensing device within a patient's coronary artery or coronary sinus or a cardiac vein. However, these methods appear to be experimental and have not been widely used clinically.

What has been needed is a method and system for accurately detecting the source of signals which cause the arrhythmia.

SUMMARY OF THE INVENTION

This invention is directed to an elongated intravascular sensing device for detecting electrical activity of a patient's heart within a vein or artery thereof, and particularly the electrical activity which causes arrhythmia.

The intravascular sensing device of the invention comprises an elongated shaft with a proximal section and a distal section, with the distal section of the shaft being configured so as to be advanceable through the patient's coronary anatomy. The distal section is provided with at least one and preferably a plurality of bipolar electrode pairs spaced along a length of the distal section. Up to 20 or more bipolar electrode pairs may be provided along the distal section of the shaft.

The shaft of the intravascular sensing device is preferably formed of a plurality of insulated electrical conductors braided or wound into an elongated tubular member, although not all of the strands which make up the tubular member need be electrical conductors. The insulation on separate conductors is exposed under each of the sensing electrodes so that an electrical connection can be made. The electrical connection may be secured by means of a suitable solder or brazing material, and the electrodes may be secured to the underlying tubular member by a suitable means such as an adhesive to ensure maintenance of electrical contact with the exposed conductors. The proximal ends of the electrical conductors are electrically connected to a multi-pin connector on the proximal end of the shaft which is configured to be connected to a receiving member in electrical communication with a display unit.

A plastic jacket, preferably a lubricious polymer such as a thermoplastic fluoropolymer, is applied to the length of the braided tubular member with a slight overlap of the jacket over the edges of the individual electrodes to prevent exposure of a sharp metallic edge which can cause damage when the elongated device is advanced through blood vessels.

The elongated device of the invention may be in the form of a guidewire which has an elongated core member disposed within tubular member formed by the braided electrical conductors. The distal section of the guidewire may have a flexible tip coil which is distal to the length on which the bipolar electrodes are mounted and which is disposed about the distal extremity of the core member. The distal end of the core member may be manually shapable by the physician to facilitate steering the distal portion of the elongated sensing device within the patient's vasculature by torquing the proximal end which extends out of the patient during the procedure. A smooth rounded tip or plug is provided at the distal end of the coil to avoid damage when being advanced through the patient's vasculature. A safety or shaping ribbon may extend from the distal end of the core member to the rounded tip in conventional guidewire fashion.

The elongated device of the invention may also be in the form of a catheter which has an elongated inner lumen extending from the proximal end to a discharge or guidewire port in the distal end of the device. The distal end of the catheter may be provided with a soft tip to minimize traumatic engagement with a blood vessel wall when being advanced therein. In one presently preferred embodiment the inner lumen of the catheter form of the device of the invention is configured to allow the passage therethrough of a conventional guidewire or a guidewire version of the device of the invention which allows signal detection at different locations within the same blood vessel or branch thereof.

When using the intravascular device of the invention, it is first introduced percutaneously or by means of a cut-down into one of the patient's major peripheral arteries or veins (e.g. the femoral vein or artery) and advanced through the patient's vasculature to one or more desired locations within the veins or arteries of the patient's heart. The distal section of the elongated device of the invention is preferably configured to be advanceable within a blood vessel having a native inner diameter of less than about one millimeter ant preferably less than 0.75 mm. A plurality of such devices may be introduced into the patient's vascular system with one or more devices within the patient's cardiac veins and one or more devices within the patient's coronary arteries.

Electrical signals from the patient's heart are received by the one or more electrode pairs on the distal section in bipolar mode and transmitted through the electrical conductors attached to the individual electrodes to multipin connectors on the proximal ends of the shafts. The position of an elongated sensing device of the invention within the arteries or veins of the patient's heart may be adjusted to optimize signal reception by the electrodes on the distal section of the device and to better detect electrical activity.

It is frequently desirable to provide a device within the patient's heart chambers with electrodes which provide pacing signals. This greatly facilitates the detection of the arrhythmogenic site or conducting pathways for electrical signals.

The elongated device of the invention provide substantially improved reception of electrical activity within the patient's heart without interference from electrical activity from other regions of the patient's heart. This improved accuracy greatly facilitates the mapping of the electrical activity which in turn allows more accurate ablation. These and other advantages will become more apparent from the following detailed description of the invention and the accompanying exemplary drawings.

BRIEF DESCRIPTION OF THE DRAWINGS

FIG. 1 is an elevational view of a guidewire embodying features of the invention.

FIG. 2 is an enlarged for longitudinal cross-sectional view of a distal portion of the guidewire show 1 in FIG. 1.

FIG. 3 is an enlarged longitudinal cross-sectional view of the distal portion of a guidewire similar to that shown in FIG. 2 but having a plurality of braided layers.

FIG. 4 is a transverse cross-sectional view of the distal portion of the guidewire shown in FIG. 3 taken along the lines 4—4.

FIG. 5 is a longitudinal cross-sectional view of an intermediate portion of the guidewire shown in FIG. 1 taken along the lines 5—5.

FIG. 6 is a longitudinal cross-sectional view of the an extension of the proximal end of the guidewire shown in FIG. 1 taken along the lines 6—6.

DETAILED DESCRIPTION OF THE INVENTION

Figure 7:
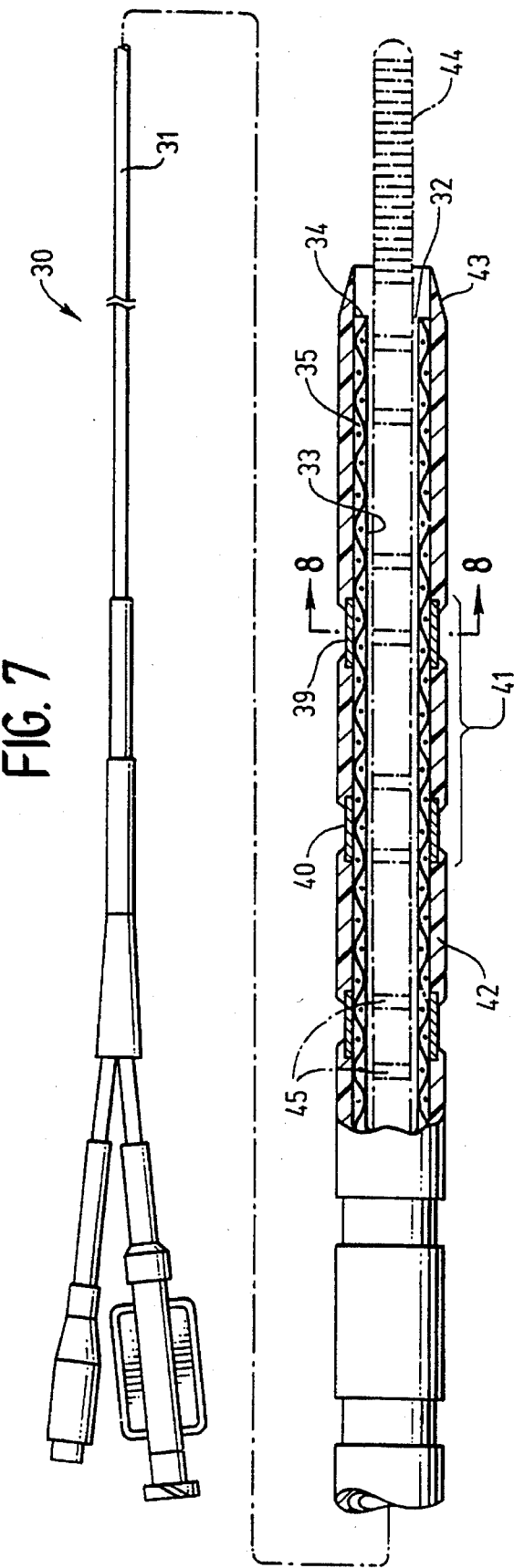
FIG. 7 is an elevational view, partially in section, of a catheter embodying features of the invention.

Reference is made to FIGS. 1–5 which schematically illustrate an embodiment of the invention wherein the elongated device 10 is the form of a guidewire. The elongated device 10 includes shaft 11 with a distal section 12 and a proximal section 13. The shaft 11 is formed of a braided tubular member 14 formed of a plurality of electrical conductors 15. The distal section 12 of the shaft 11 is provided with a plurality of bipolar electrode pairs 16, each pair of which includes electrodes 17 and 18. A core member 19 is disposed within the inner lumen of the braided tubular member 14 and extends beyond the distal end thereof. A distal coil 20 is disposed about and secured by suitable means, such as brazing, soldering or an appropriate adhesive, to the distal extremity of the core member 19 and is provided with a smooth rounded distal tip 21 formed by joining the distal tip of the coil 20 to the distal extremity of the core member 19. The distal extremity of the core member 19 may be flattened into a rectangular cross-section.

FIG. 2 illustrates a sing e braided layer with sixteen strands. However, when a higher number of electrode pairs 16 are used, e.g. sixteen or more, a plurality of braided layers may be required, as depicted in FIG. 3. As shown in this drawing the outer braided layer 22 terminates at a location proximal to that of the intermediate layer 23 and the intermediate layer terminates at a location proximal to the innermost layer 24 to facilitate securing and electrically connecting the electrodes 17 and 18 to the individual electrical conductors 15 as shown in FIG. 4. Some of the strands in the layers may not be conductors and be formed of polymer materials such as nylon.

The proximal section 13 of the shaft 11 as shown in FIG. 1 has two extensions 26 and 27 which have multi-pin connectors 28 and 29 on the proximal ends thereof with each of the electrical conductors 15 being electrically connected to a separate pin. Details of proximal extension 26 is depicted in FIG. 6. A sixteen pin connector is schematically shown in FIG. 6 but connectors having a higher or lower number of pins may be suitable.

Figure 8:
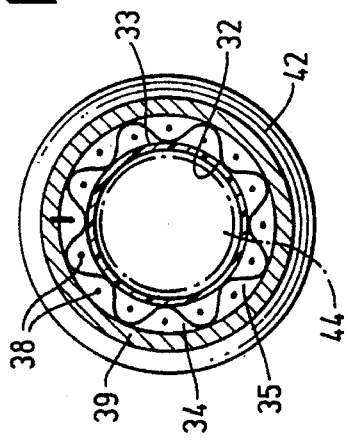
FIG. 8 is a transverse cross-sectional view of the catheter shown in FIG. 7 taken along the lites 8—8.

FIGS. 7 and 8 schematically illustrate another presently preferred embodiment of the .invention in the form of a catheter 30. In this embodiment, the catheter shaft 31 has an inner lumen 32 defined by an inner tubular element or lining 33 which is preferably formed of lubricious material such as Teflon®. A tubular member 34 is disposed about tubular lining 33 and is formed of at least one braided layer 35. A plurality of the strands making up each of the braided layers are insulated electrical conductors 38 which are electrically connected to individual electrodes 39 and 40 of electrode pairs 41 as in the previously described embodiment. While not shown in the drawing, a plurality of braided layers may be required with more than eight electrode pairs 41. As in the previous embodiment, when a plurality of braided layers are employed, the outer braided layer should terminate at a location proximal to that of the intermediate layer and the intermediate layer should terminate at a location proximal to the inner layer to facilitate securing and electrically connecting the electrodes 39 and 40 to the individual electrical conductors 38. Some of the strands in each of the Payers may be formed of other materials such as nylon. An outer jacket 42 extends the length of the shaft 31 and the portion of the jacket extending beyond the distal end of the braided tubular member 34 is tapered to provide a nontraumatic flexible distal tip 43. Is in the previously described example, the outer jacket 42 overlaps the edges of the electrodes 39 and 40 to avoid exposing a sharp metal edge when advancing the catheter through a patient's blood vessel.

The catheter 30 may be used by itself to detect electrical signals within the patient's coronary veins or arteries with the multiple electrode pairs 41 as in the previous embodiment. Additionally, the catheter may also be used to direct fluids containing cardioplegic materials such as iced saline, solutions of KCl, lidocaine, procaineamide hydrochloride and the like to areas of the patient's heart which are suspected to be the origin of or conduct the aberrant signals. If the arrhythmia stops upon the delivery of such cardioplegic agents, then the operator is assured that the artery or vein through which the agent is delivered leads toward or away from the region of the patient's heart which is to be ablated in order to terminate the arrhythmia. The signal reception by the electrode pairs 41 are essentially the same as in the previously described guidewire embodiment.

The catheter 30 may also be used in conjunction with a guidewire 44 (shown in phantom) as illustrated in FIGS. 1–5. The catheter 30 may be positioned at a first location within a coronary artery or cardiac vein of the patient with the guidewire 44, which has a plurality of bipolar electrode pairs 45 as in the previously discussed embodiment, disposed within the inner lumen of the catheter 30 and the distal section thereof extending out the port 46 in the distal end of the catheter into the patient's blood vessel. Adjustments in the relative locations of the guidewire 44 and catheter 30 can be easily made by moving the guidewire 44 through the inner lumen 32 of the catheter 30 or moving the catheter over the guidewire or both.

When using a femoral artery or femoral vein approach to the patient's heart, it is frequently helpful to utilize a guiding catheter to guide the catheter or guidewire of the invention to the coronary artery ostium or the coronary sinus ostium. Such guiding catheters have specially shaped distal tips to facilitating the seating thereof within the desired ostium, thus eliminating the trouble of directing a catheter or guidewire of the invention into the desire ostium.

The bipolar electrodes are circular bands about 0.25 to about 1 mm in width and are preferably made from conducting material which is biocompatible with the body fluids such as gold. The electrodes of the electrode pairs are spaced from each other by about 0.5 to about 2 mm, preferably about 0.75 to about 1.25 mm, and the spacing between the bipolar electrode pairs is about 2 to about 10 mm, preferably about 7 to about 8 mm.

The overall length of the intravascular devices of the invention may range from about 80 to about 300 cm, typically about 135 to about 175 cm for delivery through the femoral artery or vein and about 90 to about 120 cm for delivery through the brachiocephalic artery or internal jugular vein. If the guidewire is to be advanced through the inner lumen of the catheter it should be longer than the catheter by about 20 to about 40 cm. The distal section of the catheter is about 10 to about 50 cm in length and is configured to be readily advanceable through a patient's coronary arteries or cardiac veins. The outer diameter of the catheter should be less than about 0.055 inch (1.4 mm) and preferably about 0.035 inch (0.89 mm). The inner lumen 32 is about 0.012 to about 0.022 inch (0.3–0.56 mm) in diameter to facilitate the reception and advancement of a guidewire therethrough. The distal section of the guidewire is about 15 to about 40 cm in length and about 0.008 to about 0.022 inch (0.2–0.56 mm) in outer diameter to facilitate advancement through the coronary arteries and cardiac veins of a human being having natural diameters of less than 0.04 inch (1 mm), preferably less than 0.03 inch (0.75 mm). The distal coil on the guidewire is about 2 to about 10 cm in length and is formed of wire about 0.0003 to about 0.006 inch (0.008–0.153 mm) in diameter. The core member of the guidewire may be tapered along its distal section in a conventional guidewire construction. The flattened distal portion has a rectangular transverse cross section of about 0.002 by about 0.006 inch (0.051–0.15 mm)

To the extent not previously described, the materials of construction of the various guidewire and catheter parts may be formed of conventional materials. The electrical conductors may be electrical grade copper wire about 0.005 inch (0.13 mm) in diameter which are provided with a thin insulated jacket or coating of polyimide or other suitable insulator. The outer jacket may be a thermoplastic fluoropolymer such as THV which is available from the 3M Corporation. The distal tip coil on the guidewire form of the invention is preferably formed of platinum to facilitate fluoroscopic observation thereof within the patient, but it may be formed in whole or in part with other material such as stainless steel, titanium, palladium, niobium, iridium, rhodium and alloys thereof. The core wire of the guidewire may be formed of stainless steel or a superelastic NiTi type alloy, with the latter preferably having a stable austenite phase at body temperature and exhibiting a stress induced austenite-to-martensite phase transformation. Proximal and distal sections of the core member may be formed of different materials so as to provide a stronger proximal section for greater pushability and a more flexible distal section to facilitate passage through tortuous coronary anatomy.

Figure 9:
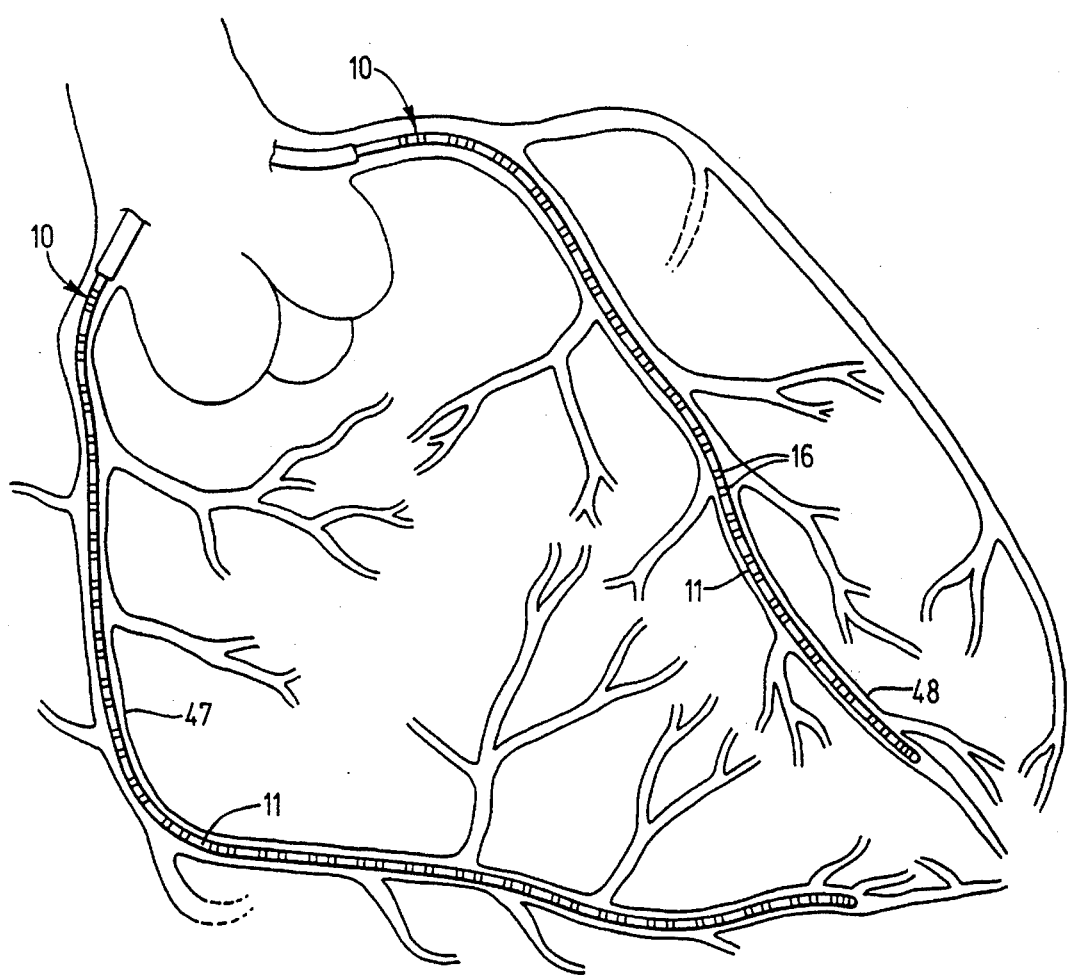
FIG. 9 is a schematic view of a patient's coronary arteries with guidewires shown in FIG. 1 disposed within the right coronary artery and the anterior interventricular branch of the left coronary arteries.

One presently preferred method of using the elongated intravascular devices of the invent on as shown in FIG. 9 wherein the distal portion 11 of the guidewires 10 such as shown in FIG. 1 are disposed within the right coronary artery 47 and the anterior interventricular branch of the left coronary artery 48. As indicated, the electrode pairs 16 on the distal portion 11 extend along a major portion of the arteries. The individual intravasular devices may be moved within the arteries as needed to optimize the signals received. While not shown in the drawings, the distal tip with the coil 20 may be shaped to facilitate entry into a side branch of the coronary artery.

Figure 10:
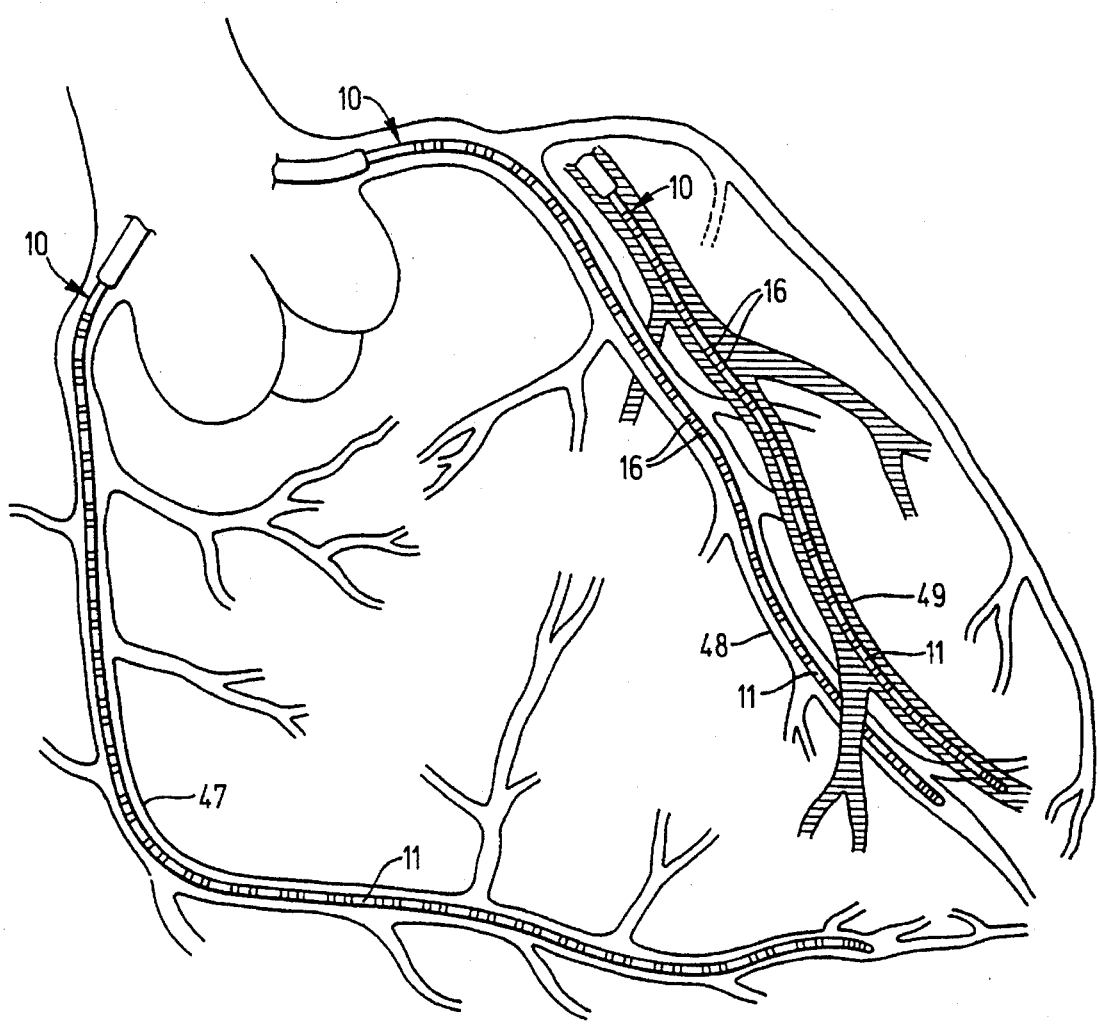
FIG. 10 is a schematic view of a patient's coronary arteries and the great cardiac vein with guidewires as shown in FIG. 1 disposed within the anterior interventricular branch of the left coronary artery and the great cardiac vein.

Another method is depicted in FIG. 10 wherein one of the elongated intravascular devices 10 of the invention are disposed within the great cardiac vein 49 and another is disposed within the anterior interventricular branch of the left coronary artery 48. A third intravascular device might also be deployed within the right coronary artery 47 as shown to provide a more comprehensive mapping of the patient's heart. As in the prior method the individual guidewires or other intravascular sensing devices may be moved within the artery or vein to better receive electrical activity.

Figure 11:
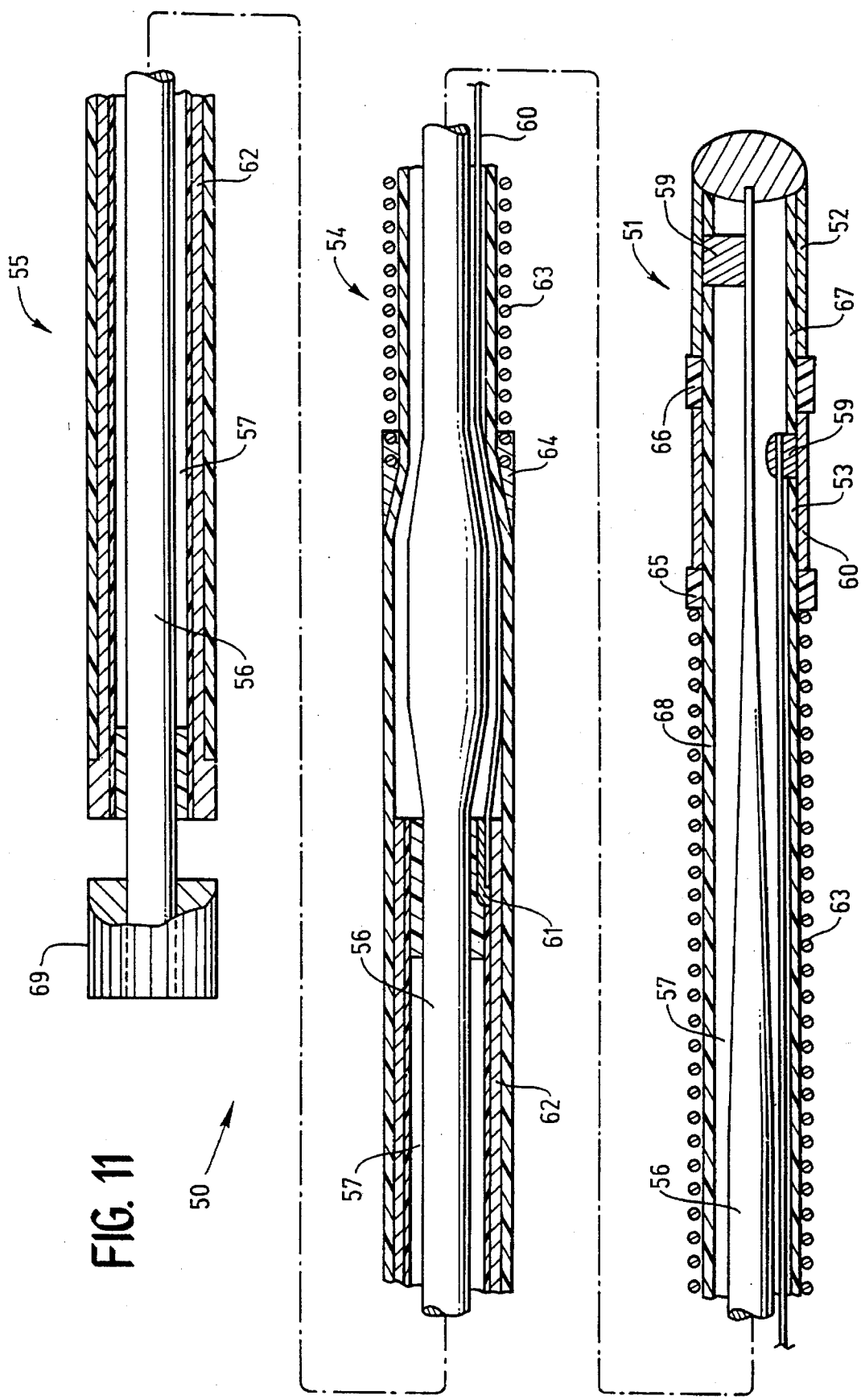
FIG. 11 is a longitudinal cross-sectional view of an alternative guidewire construction embodying features of the invention.

An alternative embodiment of the invention in the form of a guidewire 50 is shown in FIG. 11 which has a distal portion 51 with bipolar electrodes 52 and 53, an intermediate portion 54 and a proximal portion 55. A core member 56 extends through the inner lumen 57 of the guidewire 50 from the proximal end to at least the distal portion 51. The distal bipolar electrode 52 is electrically secured to the core member 56 by solder 58 and the proximal bipolar electrode 53 is secured by solder 59 to electrical conductor 60 which may be an insulated wire or ribbon. The proximal end of the electrical conductor 60 is secured by solder 61 to conductive metal tube 62 (e.g. hypotubing) which is electrically isolated from the core member 56. The exterior surface of the core member 56 and the exterior of the conductive metal tube 62 should be provided with an insulating jacket or coating to maintain the electrical isolation therebetween. The core member 56 and the conductive metal tube 62 are preferably secured together at one or more locations by an insulating adhesive to facilitate the torqueability of the overall guidewire assembly. Preferably, they are secured at least at the distal end of the metal tube 62.

A coil 63 is disposed about core member 56 proximal to the bipolar electrode pair 52 and 53 and it is secured to the core member by a suitably adhesive 64 or solder or weld. The coil 63 is preferably formed at least in part by a highly radiopaque biocompatible metal, e.g platinum, rhodium, palladium, tungsten, gold, silver or alloys thereof, to facilitate the fluoroscopic observation thereof when disposed within the vasculature of a patient. A palladium-tungsten alloy is preferred. The core member 56 and the coil 63 provide shapeability to the distal portion 51 of the guidewire 50 to facilitate advancement thereof into side branches of a patient's vasculature. An insulating member 65 is disposed between the coil 63 and the proximal bipolar electrode 53 and an insulating member 66 is disposed between electrodes 52 and 53.

An inner tubular member 67 may be disposed within the distal section to provide support to the electrodes 52 and 53 and inner tubular member 68 may be disposed within the coil 63 to likewise provide support thereto. A suitable material is thin walled polyimide tubing which is commonly employed in intravascular catheters. A torquing knob 69 is provided on the proximal end of core member 56.

The guidewire 50 may be of conventional intravascular guidewire construction. The overall length is about 150 to about 200 cm, the proximal OD of the core member 56 is typically about 0.013 inch and the distal OD about 0.006 inch which may be further reduced to 0.003 inch. The core member 56 may be ground through one or more transitions to the smaller OD sections. The core member 56 and particularly the distal portion thereof may be formed of a superelastic alloy such as NiTI which has a stable austenite phase at body temperature.

Figure 12:
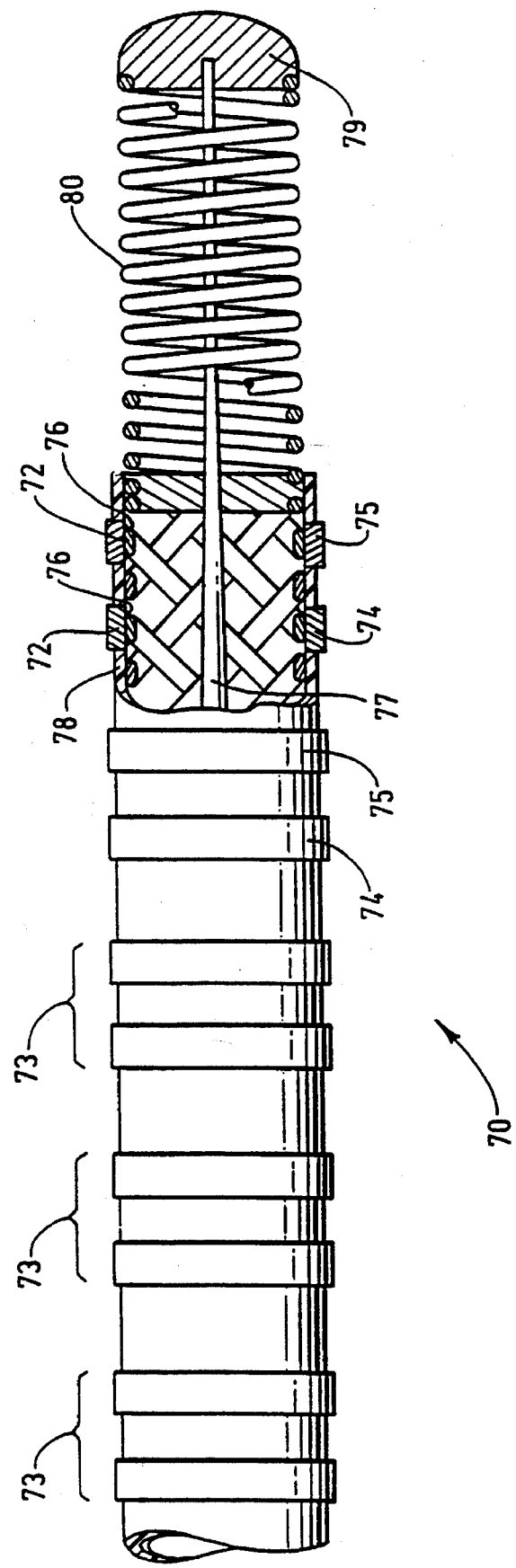
FIG. 12 is an elevational view, partially in section, of an alternative guidewire construction.

Another alternative guidewire embodiment of the invention is shown in FIG. 12. In this embodiment the guidewire 70 has a shaft 71 formed of woven or braided conductors 72 which are preferably insulated along their length and which extend to the proximal end of the shaft. A plurality of bipolar electrode pairs 73 with each pair having a proximal electrode 74 and a distal electrode 75. Each of the electrodes are electrically connected to a separate electrical conductor 72 by suitable conductive solder 76. While it is preferable that the conductors are interwoven into the tube forming the shaft 71, the conductors may be twisted or wound. In the latter case the inner and outer layers of wires would be laid out diagonally but the conductors of one layer would be laid in the opposite direction to that of the conductors in the other layer. Usually, the wound or twisted conductors are secured together by suitable adhesive, whereas with the interwoven conductors there is sufficient interlocking of the conductors that adhesives are not usually needed. An insulating jacket 78 is provided about the catheter shaft 71.

The core member 77 extends through the interior of the guidewire shaft from the proximal end to the distal end thereof where it is secured to the distal tip or plug 79 of the guidewire 70. A helical coil 80 is disposed about a distal portion of the core member 77 and is secured at its distal end to the distal tip or plug 79 and at its proximal end by adhesive 81. The coil 80 is preferably formed at least in part by a radiopaque material such as those previously discussed. The core member 77 may be configured as in the previous embodiments.

It is within the ambit of this invention that the intravascular sensing device be introduced into a femoral artery or a femoral vein (or other convenient body access site) and be advanced through the patient's vasculature to the coronary veins or arteries. Once the intravascular device is situated in the proper location in the coronary vasculature, electrical activity may be received in any way that is appropriate for the specific situation. The catheter or guidewire may be moved to another location and another set of signals received. It should be apparent that since each electrode mounted on the distal section of the sensing device is individually brought out via the woven wires or filaments to the electrical connection at the proximal end, that each electrode may be used in conjunction with any other electrode in a bipolar mode. The sensing devices may be used in multiples, e.g., a sensing device in each of the major coronary veins and arteries, as shown in FIGS. 9 and 10, to provide an overall and complete electrical map of the heart. In this way, arrhythmia foci may be readily located and therapeutic action taken.

Figure 13:
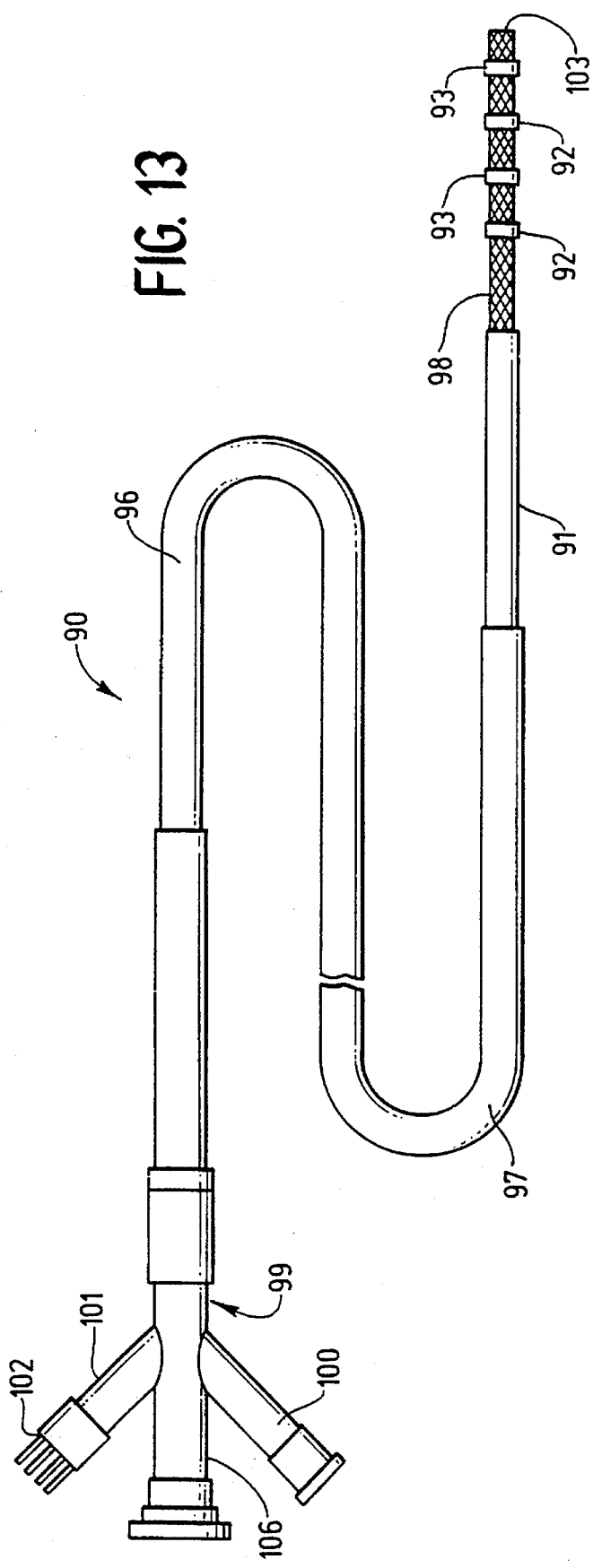
FIG. 13 is an elevational view, partially in section, of an alternative catheter construction embodying features of the invention.
Figure 14:
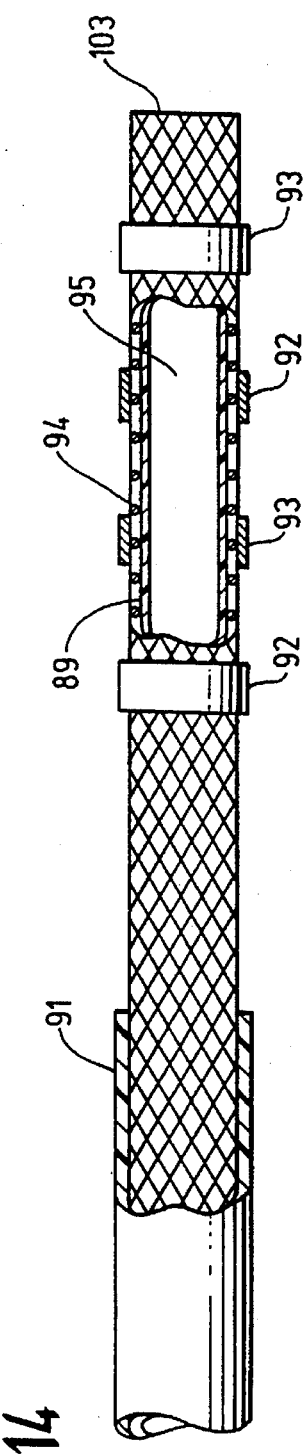
FIG. 14 is an enlarged elevational view partially in section of the distal portion of the catheter shown in FIG. 13.

FIGS. 13 and 14 illustrate a catheter assembly 90 which embodies an additional aspect of the present invention directed to an intravascular catheter 91 for sensing electrical activity within a patient's coronary or cardiac blood vessels. As in the prior embodiments the bipolar electrodes 92 and 93 are electrically connected to individual electrical conductors 94 which are woven or wound to form the tubular shaft 95 of the catheter 91. All of the strands which are wound to form the shaft 95 need not be conductors 94 but may be strands of polymeric materials such as polyethelene terephthalate Dacron®, nylon, silk or other natural or synthetic polymeric material. When there are more than 16 electrodes and thus more than 16 electrical conductors, multiple woven layers may be employed. FIG. 14 illustrates in more detail the connection of electrical conductors 94 to the individual electrodes 92 and 93. The electrical conductors 94 are typically electrical grade copper wires of suitable outer diameter such as about 0.004 to about 0.01 inch (0.10–0.25 mm). The conductors 94 may be formed of other conducting materials such as silver, gold and platinum. A suitable insulating material to coat the conductors 94 is polyimide which minimizes cross talk and which can be applied in very thin layers. As in the other embodiments of the invention the conductors 94 may be woven or merely wound, but preferably are woven.

The inner lumen 95 of the catheter 91 is configured to slidably receive a guidewire to facilitate the advancement of the catheter over the guidewire and preferably has at least in the distal portion thereof a diameter about 0.002 to about 0.005 inch (0.051–0.127 mm) greater than the guidewire which is to be disposed therein. For guidewire having OD of about 0.016 to about 0.018 inch (0.41–46 mm), the inner lumen 97 would be about 0.018 to about 0.023 inch (0.46–0.58 mm). The OD of the catheter may range from about 0.03 to about 0.1 inch (0.76–2.54 mm) but preferably is about 0.03 to about 0.05 inch (0.076–1.27 mm), particularly 0.035 to about 0.040 inch (0.89–1.02 mm), The proximal portion 96 of the catheter 91 makes up about 70 to about 95% of the total length of the catheter with the intermediate portion 97 and the distal portion 98 which has the sensing electrodes 92 and 93 being the remainder. Preferably the catheter 91 has decreasing stiffness from the proximal portion 96 to the intermediate portion 97 and the distal portion 98 to facilitate the advancement of the catheter 91 within the patient's vasculature. The exterior surface of the catheter 91 and the surface defining inner lumen 95 may be formed of lubricous materials or hydrophilic materials which become lubricious when contacting aqueous based fluids. Polysulfones and polyfluoroalkanes are examples of suitable lubricious polymers and polyvinylpyrrolidone, polyethylene oxide and acrylate-based polymers of examples of suitable hydrophilic polymers.

The proximal end of the catheter 91 may be provided with a multiple arm adapter 99 as shown in FIG. 13 with one arm 100 which is configured to receive a syringe for delivering fluid into the inner lumen 97 and a second arm 101 which is provided with an electrical connector 102 which is electrically connected to the electrical conductors 94. The central arm 106 facilitates entry of a guidewire (not shown) into the inner lumen 97. The catheter 91 may be advanced into position within the patient's vascular system, i.e. either the coronary arteries or the cardiac veins, over a guidewire which may or may not have electrodes in accordance with the invention to detect electrical activity therein. If the guidewire over which the catheter is advanced into the patient's vasculature does not have sensing electrodes on its distal extremity, it may be withdrawn when the catheter is in its desired position and a guidewire such as shown in FIG. 4 may be advanced through the inner lumen 95 of the catheter 91 and off the port 103 in the distal end of the catheter to a more distal position with the blood vessel.

Once the arrhythmogenic site or conductive pathway causing an arrhythmia is located by detecting the electrical activity, means can be advanced through the inner lumen 95 of a catheter of the invention to occlude an arterial passageway which feeds the arrhythmogenic site or conductive pathway so as to terminate the arrhythmia.

Figure 15:
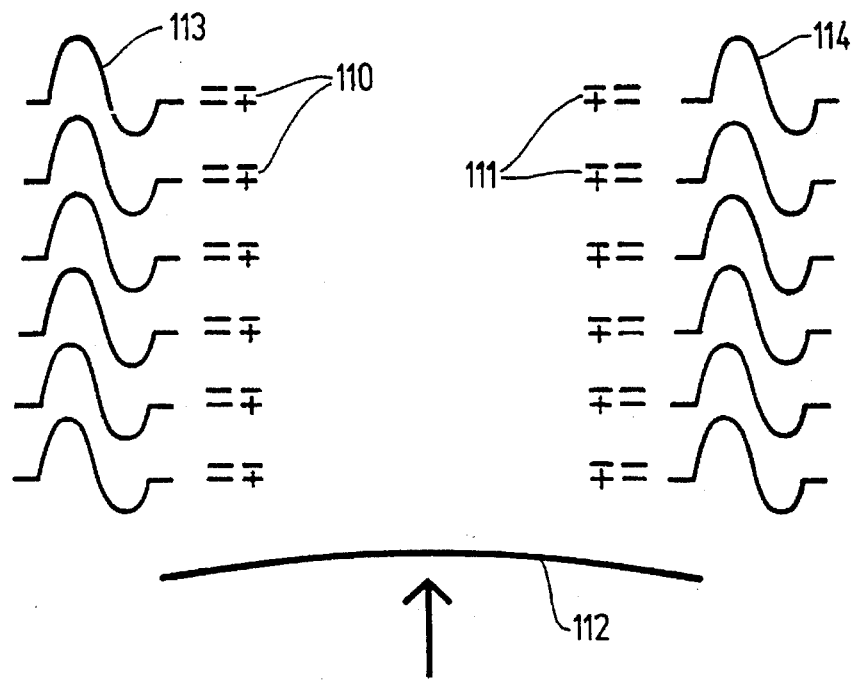
FIG. 15 is a schematic representation of responses of bipolar electrodes on separated intravascular devices from an essentially planar wave front.

FIG. 15 represents an idealized output from a plurality of electrode pairs 110 and 111 on two separate intravascular devices (not shown) disposed in different, generally parallel coronary blood vessels, e.g. a coronary artery and the companion vein, to a nearly planar wave front 112 approaching on end to the intravascular devices. The bipolar response 113 and 114 to the wave front 111 from each electrode pair 110 and 111 is shown adjacent thereto, and as indicated, all of the responses are essentially identical, except for the time-of-occurrence, because the wave front reaches all of the electrodes at the same angle. Changes in tissue properties, e.g. due to an infarct, adjacent the catheters may retard the passage of the wave front and as a result distort the shape of the output.

Figure 16:
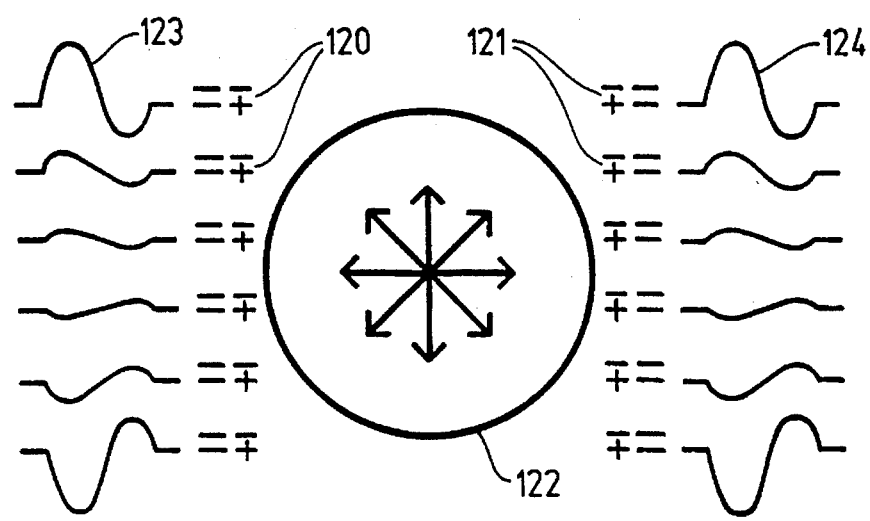
FIG. 16 is a schematic representation of bipolar electrodes on separated intravascular devices from a circular wave front.

FIG. 16 represents an idealized response from a plurality of electrode pairs 120 and 121 on two separate intravascular devices (not shown) disposed in different generally parallel coronary blood vessels, as in FIG. 16, but the wave front 122 originates from a site between and in close proximity to the catheters. The idealized wave front 121 is circular and the size and polarity of the responses 123 and 124 to the expanding wave front varies according to the angle of incidence between the wave front and the electrode pair. An arrhythmogenic site would create a less than ideal wave front which can be readily detected by the plurality of electrodes 120 and 121.

The time of occurrence and directional information obtained from the response from the wave front may be used to determine the origin of the ectopic beat.

EXAMPLE

A guidewire was constructed using a woven tubular braid of sixteen insulated electrical conducting wires, eight woven counterclockwise and eight woven clockwise. Gold metal electrodes 0.01 inch in width were mounted onto the distal end of the shaft about 0.5 inch (12.7 mm) apart with each attached to one of the electrical conducting wires. The overall length of the guidewire was about 240 cm. An eight connector DIN plug was installed at the proximal end of the guidewire. The guidewire assembly was 0.018 inch (0.46 mm) in diameter at the distal end, 0.026 inch (0.66 mm) in diameter at the midsection, and 0.032 inch (0.81 mm) at the more proximal end.

Figure 17:
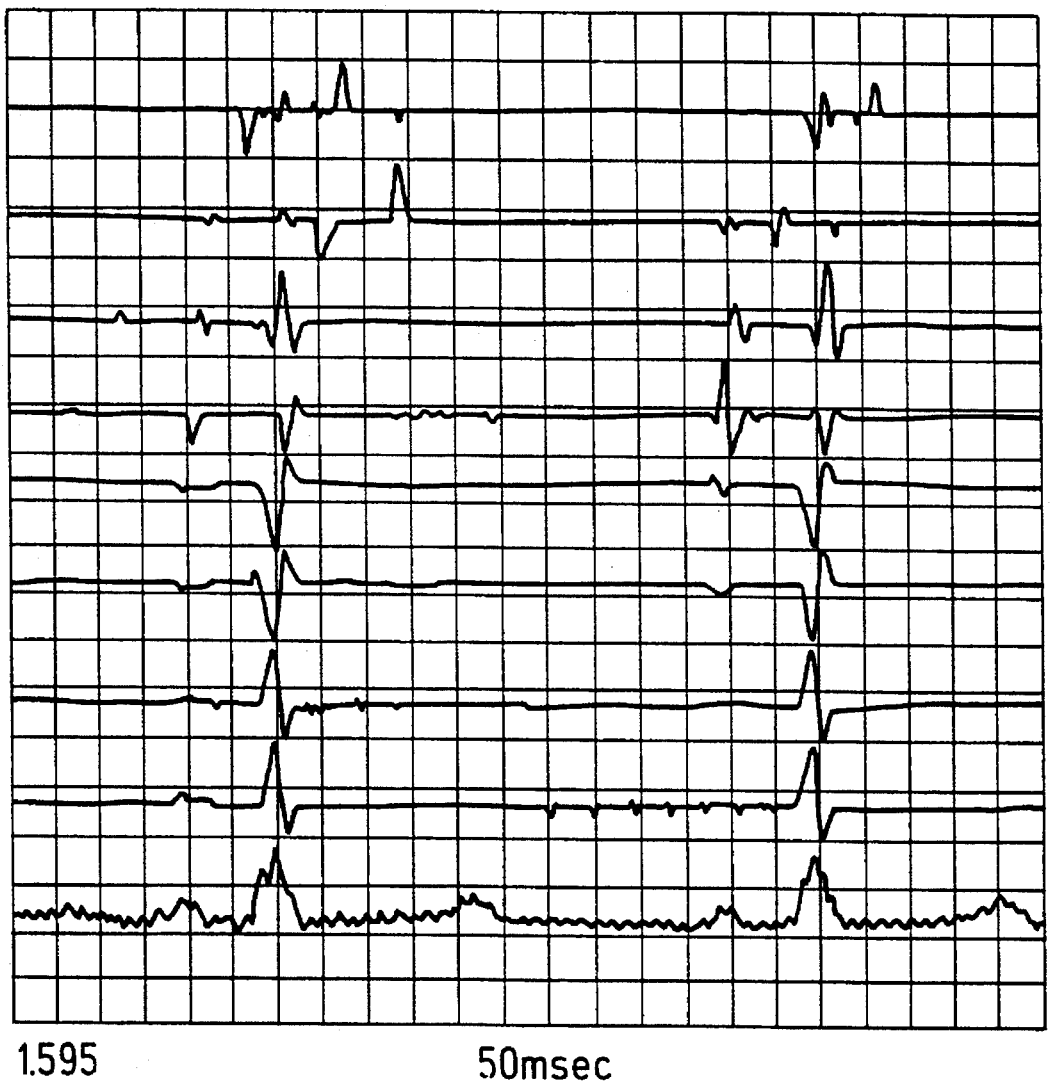
FIG. 17 is an electrocardiogram using a guidewire to detect electrical activity on the bipolar mode.

The guidewire was introduced into the coronary artery of a live dog using a 7 French coronary guide catheter. A pacer lead having four electrodes was disposed within the heart chamber and was used to pace a ventricular beat so that the electrical activity as a result of that pacing could be monitored intravascularly using the guidewire of the invention. FIG. 17 is an electrocardiogram produced using the guidewire of the invention which depicts two pulses from that animal test in bipolar mode.

The present invention has been described herein in terms of certain preferred embodiments but various modifications may be made to the present invention without departing from the scope thereof.

What is claimed is:

1. An elongated intravascular device for detecting electrical activity within a blood vessel of a patient's heart, comprising:
    a) an elongated shaft having proximal and distal sections with the distal section being configured to be advanceable through a coronary artery or a cardiac vein of a patient's heart;
    b) at least one pair of sensing electrodes mounted on the distal section with the electrodes being electrically connected to separate electrical conductors which extend to the proximal section of the elongated shaft; and
    c) a manually shapable flexible guiding tip which extends axially in a distal direction from the sensing electrodes on the distal section and which is configured to be readily advanced through a blood vessel of the patient's heart.

2. The intravascular sensing device of claim 1 wherein the elongated shaft is a tubular member formed by strands which include a plurality of insulated electrical conductors.

3. The intravascular sensing device of claim 2 where the strands are braided into the tubular member.

4. The intravascular device of claim 2 wherein the tubular member has an inner lumen extending therein configured to slidably receive a guidewire.

5. The intravascular device of claim 4 wherein the inner lumen has a diameter of less than about 0.022 inch.

6. The intravascular device of claim 2 wherein the tubular member has a tubular lining which defines an inner lumen extending therein.

7. The intravascular device of claim 6 wherein the tubular lining is formed of a lubricous material.

8. The intravascular device of claim 7 wherein the lubricous material is a fluoropolymer.

9. The intravascular sensing device of claim 1 wherein a plurality of electrode pairs are mounted on the distal shaft section.

10. The intravascular device of claim 9 wherein there is a spacing of about 2 to about 10 mm between adjacent electrode pairs.

11. The intravascular device of claim 9 wherein there is a spacing of about 5 to about 8 mm is between adjacent electrode pairs.

12. The intravascular device of claim 1 wherein there is a spacing of about 0.25 to about 2 mm between the electrodes of said at least one electrode pair.

13. The intravascular device of claim 1 wherein there is a spacing of about 0.5 to about 1.25 mm between the electrodes of an electrode pair.

14. The intravascular device of claim 1 wherein the electrodes are circular bands of electrical conducting materials having widths of about 0.25 to about 1 mm.

15. The intravascular device of claim 1 wherein the shaft has an inner lumen extending therein, an elongated core member is disposed within the inner lumen of the shaft and a distal extremity of the elongated core member forms at least in part the manually shapable guide tip.

16. The intravascular device of claim 15 wherein the guide tip includes a flexible member which is disposed about the distal extremity of the core member.

17. An elongated intravascular catheter for detecting signals within a blood vessel of a patient's heart and which is advanceable over a guidewire, comprising:
 a) an elongated catheter shaft having proximal and distal ends, a port in the distal end and an inner lumen extending therein to and in communication with the port in the distal end and a distal section being configured to be advanceable through a vein or artery of a patient's heart over a guidewire slidably disposed within the inner lumen;
 b) a plurality of bipolar sensing electrode pairs mounted on and longitudinally spaced along a length of the distal section; and
 c) a plurality of electrical conductors extending along the catheter shaft with each sensing electrode being electrically connected to a separate electrical conductor.

18. The elongated intravascular catheter of claim 17 wherein the shaft comprises a tubular member formed from a plurality of the electrical conductors.

19. The elongated intravascular catheter of claim 18 including an outer jacket disposed about and secured to an exterior portion of the tubular member.

20. The elongated intravascular catheter of claim 18 wherein the electrical conductors are braided.

21. The elongated intravascular catheter of claim 17 wherein the catheter shaft has a proximal end and at least one multi-pin electrical connector on the proximal end which is configured to be connected to a receptor and which has individual connector pins electrically connected to separate electrical conductors.

22. The intravascular sensing device of claim 21 wherein a jacket is disposed about and secured to an exterior portion of the tubular member.

23. An elongated intravascular device for detecting electrical activity of a patient's heart from within a blood vessel thereof, comprising:
 a) an elongated shaft having proximal and distal sections, the distal section being configured to be advanceable through a vein or artery of a patient's heart;
 b) a plurality of bipolar electrode pairs mounted on and longitudinally spaced along a length of the distal section;
 c) a plurality of electrical conductors within the shaft, with each sensing electrode electrically connected to a separate electrical conductor;
 d) an outer jacket disposed about and secured to an exterior portion of the shaft; and
 e) a core member extending within the elongated shaft and forming an least in part a shapable distal tip.

24. The elongated intravascular device of claim 23 including a coil disposed about and secured to a portion of the core member which forms the shapable distal tip.

25. An elongated intravascular sensing device for detecting electrical activity of a patient's heart from within a coronary artery or cardiac vein, comprising:
 a) an elongated shaft having proximal and distal sections, with the distal section being configured to be advanceable through a vein or artery of a patient's heart and the shaft including a tubular member formed of braided strands which include a plurality of insulated electrical conductors,
 b) a plurality of sensing electrodes mounted on a length of the distal section with the electrodes being secured to the tubular member formed of braided strands and each sensing electrode being electrically connected to a separate electrical conductor, and
 c) at least one electrical connector on a proximal end of the shaft which has separate electrical connecting means connected to the individual electrical conductors electrically connected to the sensing electrodes.

26. The elongated intravascular sensing device of claim 22 wherein the distal section of the elongated shaft has a shapeable flexible guiding tip extending distal to the plurality of electrodes on the distal section of the elongated shaft.

27. An intravasular device for detecting electrical signals from within a patient's heart to facilitate determining where the signals originate, comprising:
 a) an elongated shaft having a proximal shaft section, a distal shaft section which is much shorter and more flexible than the proximal shaft section and which is configured to be readily advanced through a blood vessel of the patient's heart and a shapable flexible guiding tip which extends axially in a distal direction from the distal shaft section and which is configured to be readily advanced through a blood vessel of the patient's heart;
 b) at least one pair of bipolar sensing electrodes spatially disposed on the distal shaft section proximal to the flexible guiding tip which are adapted to receive electrical signals of the patient's heart from within a blood vessel of the patient's heart; and
 c) a plurality of electrical conductors, each of which is electrically connected to a separate bipolar sensing electrode on the distal shaft section, each of which extends to a proximal extremity of the elongated shaft and each of which is adapted to transfer electrical signals received by the sensing electrode connected thereto to means for displaying representations of the electrical signals received by the sensing electrodes in a bipolar mode.

28. An elongated intravascular device for detecting electrical signals from within a coronary artery or a cardiac vein of a patient's heart, comprising:

an elongated tubular shaft having a proximal section, a distal section and an inner lumen extending therein, the distal section being formed at least in part by a plurality of woven, individually insulated conductors extending proximally from the distal section to the proximal section and being configured to readily pass through a coronary artery or a cardiac vein;

a plurality of sensing electrodes spaced apart from each other on the distal section with each electrode being electrically connected to an individual insulated conductor, and a core member disposed within the inner lumen of the tubular shaft having a distal portion which forms at least in part a shapable distal tip on the distal section distal to the sensing electrodes.

29. The intravascular device of claim 28 having a coil disposed about the distal portion of the core member.

30. The intravascular device of claim 28 wherein the distal section of the tubular shaft has an outer diameter of not more than about 0.020 inch.

31. The intravascular device of claim 28 having an exterior coating on the tubular shaft extending from a proximal end thereof distally to the sensing electrodes.

32. The intravascular device of claim 31 in which the coating is selected from the group of consistence of polytetrafluoroethylene, polyethylene, polypropylene, polybutene, polyurethane, polyvinylpyrrolidone, polyethylene oxide, hyaluronic acid polymers, mixtures thereof and copolymers thereof.

33. An elongated intravascular device for detecting electrical signals from within a coronary artery or cardiac vein of a patient's heart, comprising:

a) an elongated torquable tubular shaft having a proximal portion, a distal portion which is much shorter and more flexible than the proximal portion and which is configured to readily pass through a coronary artery or a cardiac vein and a plurality of interwoven, individually insulated electrical conductors forming a cylindrical wall of the distal portion; and b) a plurality of sensing electrodes spaced apart from each other on the distal portion of the elongated tubular shaft, each of the electrodes being electrically connected to an individual insulated electrical conductor.

34. The intravascular device of claim 33 wherein the cylindrical wall formed by the electrical conductors defines an inner lumen and a elongated core member extends through the inner lumen defined by the cylindrical wall.

35. The intravascular device of claim 33 wherein the distal portion of the core member has a diameter of about 0.005 to about 0.01 inch.

36. The intravascular device of claim 33 wherein the distal portion of the elongated shaft is about 0.01 to about 0.02 inch in diameter.

37. The intravascular device of claim 33 wherein the sensing electrodes are circular bands.

38. The intravascular device of claim 37 wherein the sensing electrodes are formed of a material selected from the group consisting of platinum, palladium, gold and silver.

39. The intravascular device of claim 33 wherein the tubular shaft has a maximum diameter of not more than about 0.04 inch.

40. The intravascular device of claim 33 wherein the tubular shaft has an intermediate section disposed between the proximal and distal sections.

41. An elongated steerable intravascular device for detecting electrical signals from within a coronary artery or cardiac vein of a patient's heart, comprising a) a torqueable elongated tubular shaft having
a proximal shaft portion,
a distal shaft portion which is much shorter and more flexible than the proximal shaft portion and which has an outer diameter configured to readily pass though a patient's coronary artery or cardiac vein, and
a plurality of individually insulated electrical conductors extending from the distal shaft portion to the proximal shaft portion and forming at least the distal portion of the elongated tubular shaft; and b) a plurality of sensing electrodes spaced apart from each other on the distal shaft portion, each electrode being electrically connected to an individual insulated electrical conductor.

42. The elongated steerable intravascular device of claim 41 wherein the proximal and digital shaft portions of the tubular shaft are formed of interwoven, separately insulated electrical conductors.

43. The elongated steerable intravascular device of claim 42 wherein the proximal and distal shaft portions of the tubular shaft are formed of wound individually insulated electrical conductors.

44. The elongated steerable intravascular device of claim 41 wherein an elongated core member extends within an inner lumen of at least the distal shaft portion of the tubular shaft.

45. The elongated steerable intravascular device of claim 44 wherein the elongated core member lumens a shapable guide tip to facilitate entry thereof into a branch cardiac vein or coronary artery within the patient's heart.

46. The elongated steerable intravascular device of claim 45 wherein the shapable guide tip of the core member has a coil disposed about and secured thereto.

47. An elongated intravascular device for detecting electrical activity of a patient's heart from within a blood vessel of the patient's heart, comprising:

a) an elongated shaft having a proximal portion and a distal portion which is much shorter and more flexible than the proximal portion, at least the distal portion being formed by a plurality of woven, individually insulated, electrical conductors; and b) a plurality of sensing electrodes longitudinally spaced apart from each other on the distal portion of the elongated shaft, each electrode being electrically connected to an individual insulated electrical conductor forming the distal shaft portion.

48. The elongated intravascular device of claim 47 wherein the elongated shaft has a shapeable flexible guiding tip extending distal to the distal portion of the elongated shaft.

* * * * *

UNITED STATES PATENT AND TRADEMARK OFFICE
CERTIFICATE OF CORRECTION

PATENT NO. : 5,509,411
DATED : April 23, 1996
INVENTOR(S) : Laszlo Littmann et al.

It is certified that error appears in the above-indentified patent and that said Letters Patent is hereby corrected as shown below:

Column 12, line 16, after "forming" delete "an" and insert --at.

Column 13, line 30, after "group" delete "of consistence" and insert --consisting--.

Column 13, line 51, after "and" delete "a" and insert --an--.

Column 14, line 9, after "comprising" insert --:--.

Column 14, line 40, after "member" delete "lumens" and insert --has--.

Signed and Sealed this

Nineteenth Day of November, 1996

Attest:

BRUCE LEHMAN

Attesting Officer

Commissioner of Patents and Trademarks